United States Patent [19]

Froot

[11] 4,406,844

[45] Sep. 27, 1983

[54] FABRICATION OF SEMICONDUCTOR MODULES WITH CERAMIC SUBSTRATES AND DETECTION OF RESIDUAL GLASS

[75] Inventor: Howard A. Froot, Hartsdale, N.Y.

[73] Assignee: International Business Machines Corporation, Armonk, N.Y.

[21] Appl. No.: 313,072

[22] Filed: Oct. 19, 1981

[51] Int. Cl.$^3$ .............................................. C09K 1/10
[52] U.S. Cl. ...................................... 264/21; 264/22; 264/61; 264/63; 264/67
[58] Field of Search ...................... 264/21, 22, 63, 61, 264/67

[56] References Cited

U.S. PATENT DOCUMENTS

| | | | |
|---|---|---|---|
| 2,635,329 | 4/1953 | de Forest et al. | 29/148 |
| 2,945,128 | 7/1960 | Sun | 264/21 |
| 3,117,227 | 1/1964 | Pollack | 250/71 |
| 3,386,920 | 6/1968 | Alburger | 252/301.2 |
| 3,718,601 | 2/1973 | Dentai | 264/61 |
| 3,995,157 | 11/1976 | Holub et al. | 250/302 |
| 4,313,900 | 2/1982 | Gonzales | 264/61 |

*Primary Examiner*—John A. Parrish
*Attorney, Agent, or Firm*—Nathan N. Kallman; Otto Schmid, Jr.

[57] ABSTRACT

To detect residual glass, such as appears at semiconductor chip pads and via holes during the fabrication of alumina/glass ceramic substrates that are used as supports for the semiconductor devices, the glass used for forming the ceramic substrates is doped with a rare earth oxide. During the manufacturing process, the ceramic structures are irradiated after firing with radiation of wavelengths in the range 350–500 nanometers to induce the glass to fluoresce, thereby revealing the residual glass on the surface of the metallic interconnector pads. If residual glass is present, the parts are reworked, or scrapped if necessa

9 Claims, No Drawings

FABRICATION OF SEMICONDUCTOR MODULES WITH CERAMIC SUBSTRATES AND DETECTION OF RESIDUAL GLASS

DESCRIPTION

1. Technical Field

This invention relates to a process for detecting residual glass during fabrication of alumina/glass ceramic substrates employed for supporting semiconductor devices.

An object of this invention is to provide a nondestructive process for determining the presence of residual glass in a semiconductor module formed with an alumina/glass ceramic substrate.

2. Background Art

At present, in the manufacture of semiconductor devices, ceramic substrates are employed for supporting the semiconductor element. During the manufacturing process, the ceramic substrate experiences shrinkage, which may be as high as 17%. The shrinkage is closely controlled because it affects the locations of the semiconductor pad connections which must be located at precise positions. To alleviate this problem of shrinkage, a mixture of alumina and glass is added to the metallic conductive paste used in the upper layers of the multilayer ceramic substrate.

However, it has been observed that the glass migrates between from adjacent layers into and out of the metal filled via holes that have been formed in the structure, and the glass moves by capillary action through the capillaries in the metal filling the via holes to the surface of the semiconductor pad connections. If there is a significant quantity of glass on the pad surfaces, then it becomes difficult to plate conductive metals, such as gold, to make suitable electrical connections to the conductive elements in the via holes and to the pad. The detection of such glass residue, which is very thin, by mere visual inspection or simple detection means is not feasible.

The presence of excessive residual glass films on the surface of the substrate pads that the semiconductor is joined to has resulted in significant yield losses due to the inability of proper nondestructive detection.

DISCLOSURE OF THE INVENTION

In an implementation of this invention, a composition of ceramic powder, including alumina and a borosilicate glass frit, for example, is ball milled into a slurry, cast to produce green ceramic sheets, as is well known in the semiconductor art and then sintered at a high temperature. The green sheets are processed into the shape of substrates that are used for supporting semiconductor chips and electronic circuitry. To this end, the ceramic substrates are die punched to form via holes in a desired pattern. A mixture of alumina, glass frit and molybdenum in an organic binder is then screened onto the substrate to deposit a conductive pattern. The mixture, which is a conductive paste, permeates and fills the via holes, thereby enabling the provision of electrical connections to the semiconductor chip pads. The conductive mixture provides electrical paths between the top and bottom surfaces of the green sheet and affords connections to the several circuit elements disposed on the ceramic substrate. The green sheet is sintered and vapor blasted to remove residual glass from its surface.

In accordance with this invention, the glass grit used for forming the green sheet, and the glass frit used for the paste to fill the via holes, are doped with a rare earth oxide that fluoresces under applied radiation of a selected range of wavelengths. In a preferred embodiment, the glass grit used for the green sheet and the glass frit used for the paste to fill the via holes are mixed with samarium oxide. The rare earth oxide constitutes about 1% of the glass material prior to mixture with the alumina, or with the alumina and molybdenum.

Prior to deposition of the semiconductor chips onto the processed ceramic substrate, the substrate is subjected to radiation in the range of 350-500 nanometers. The radiation is applied directly to the surface of the substrate, and visual inspection is made through a microscope. The samarium oxide doped glass will fluoresce in an orange color, and a clear indication of the migration, disposition and location of residual glass is obtained. If the surface of the ceramic substrate contains an undesirable amount of residual glass that would prohibit the effective plating of conductive leads on the surface of the substrate, the substrate is vapor blasted to remove such residual glass. A second inspection of the substrate is made under the exciting radiation to determine whether the substrate has been made free of residual glass. Rework by vapor blasting is performed, as many times as economically and practically feasible, and if not successful in removal of the residual glass, the part is discarded.

It is apparent that the specific color observed and its spectrum are characteristic of the particular rare earth used. As alternatives to the $Sm_2O_3$, $Eu_2O_3$ may be used for doping the glass and would fluoresce lavender in response to the same spectrum of radiation, i.e., 350–500 nanometers; or $Dy_2O_3$ which would fluoresce yellow, may be used.

After the residual glass has been removed from the surface of the substrate, a pattern of conductive elements, which may be formed from gold, is plated onto the metallic semiconductor substrate interconnector pads. Subsequently, semiconductor chips are deposited on the substrate so that the integrated circuits are in proper electrical connection with the conductive elements.

The nondestructive process of detection of residual glass during the manufacture of semiconductor modules with ceramic substrates allows the rework, or discard of those assemblies having an excessive amount of residual glass, with the result of improved yield and reduction in cost.

What is claimed is:

1. A nondestructive method for determining the presence of residual glass during the manufacture of alumina ceramic substrates comprising the steps of:
   preparing a mixture comprising ceramic forming alumina particles and glass doped with a rare earth oxide that fluoresces in response to selected wavelengths of radiation;
   forming a green sheet containing a binder having said ceramic forming alumina particles and doped glass material;
   firing said green sheet to produce a ceramic substrate; and
   irradiating said fired structure with radiation of said selected wavelengths to induce fluorescence in said doped glass material for determining the presence of residual glass on predetermined areas of said substrate.

2. A nondestructive method as in claim 1, wherein said rare earth oxide is from the group of samarium oxide, europium oxide or dysprosium oxide.

3. A nondestructive method as in claim 1, wherein said radiation has a wavelength in the range of 350-500 nanometers.

4. A nondestructive method as in claim 1, wherein said glass is a borosilicate.

5. A nondestructive method as in claim 1, wherein said green sheet is formed in one of said predetermined areas with via holes, and a paste mixture of alumina, doped glass frit and molybdenum is screened onto a surface of said ceramic substrate so that said paste permeates said via holes.

6. A nondestructive method as in claim 1, wherein said green sheet is formed with via holes, and a paste mixture of alumina, doped glass frit and tungsten is screened onto a surface of said ceramic substrate so that said paste permeates said via holes.

7. A nondestructive method as in claim 1, including the step of plating in a second of said predetermined areas, a conductive pattern on a surface of said ceramic substrate.

8. A nondestructive method as in claim 7, wherein said substrate includes metallic interconnector pads, and said step of plating a conductive pattern on a surface of said ceramic substrate includes the step of plating a pattern of conductive elements onto said metallic substrate interconnector pads.

9. A nondestructive method as in claim 1, including the step of vapor blasting said ceramic substrate to remove residual glass.

* * * * *